(12) United States Patent
Murata

(10) Patent No.: US 8,710,066 B2
(45) Date of Patent: Apr. 29, 2014

(54) AQUEOUS COMPOSITION WITH AGENTS TO INHIBIT WATER EVAPORATION

(75) Inventor: Takeshi Murata, Odawara (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/700,322

(22) PCT Filed: May 26, 2011

(86) PCT No.: PCT/JP2011/062062
§ 371 (c)(1),
(2), (4) Date: Nov. 27, 2012

(87) PCT Pub. No.: WO2011/149006
PCT Pub. Date: Dec. 1, 2011

(65) Prior Publication Data
US 2013/0096205 A1    Apr. 18, 2013

(30) Foreign Application Priority Data

May 27, 2010    (JP) .................. 2010-121631

(51) Int. Cl.
*A61K 31/506*    (2006.01)

(52) U.S. Cl.
USPC ............................................. 514/275

(58) Field of Classification Search
None
See application file for complete search history.

(56) References Cited

U.S. PATENT DOCUMENTS

| | | |
|---|---|---|
| 3,146,059 A | 8/1964 | Suzuki et al. |
| 6,090,395 A | 7/2000 | Asmus et al. |
| 6,534,069 B1 | 3/2003 | Asmus et al. |
| 2002/0160029 A1 | 10/2002 | Asmus et al. |
| 2004/0071748 A1 | 4/2004 | Asmus et al. |
| 2006/0121071 A1 | 6/2006 | Asmus et al. |
| 2006/0139426 A1* | 6/2006 | Doi ............................. 347/100 |
| 2006/0172059 A1 | 8/2006 | Takeuchi et al. |
| 2006/0263396 A1 | 11/2006 | Asmus et al. |
| 2010/0331422 A1 | 12/2010 | Asmus et al. |

FOREIGN PATENT DOCUMENTS

| | | |
|---|---|---|
| JP | 49 121788 | 11/1974 |
| JP | 1 266844 | 10/1989 |
| JP | 11 508253 | 7/1999 |
| JP | 2000 265098 | 9/2000 |
| JP | 2001 181543 | 7/2001 |
| JP | 2003 321321 | 11/2003 |
| JP | 2008 81472 | 4/2008 |
| JP | 2011 231043 | 11/2011 |
| JP | 2011 256117 | 12/2011 |
| JP | 2012 1527 | 1/2012 |
| TW | 200501893 A | 1/2005 |
| WO | 2004 056216 | 7/2004 |

OTHER PUBLICATIONS

Berthod, A. et al., "Polyoxyethylene alkyl ether nonionic surfactants: physicochemical properties and use for cholesterol determination in food", Talanta 55 (2001), p. 69-83.*
http://www.chemicalland21.com/specialtychem/perchem/nonylphenol%20ethoxylate.htm.*
U.S. Appl. No. 13/702,484, filed Dec. 6, 2012, Murata.
International Search Report Issued Aug. 16, 2011 in PCT/JP11/62062 Filed May 26, 2011.

* cited by examiner

*Primary Examiner* — Melenie McCormick
*Assistant Examiner* — Jeanmarie Calvillo
(74) *Attorney, Agent, or Firm* — Oblon, Spivak, McClelland, Maier & Neustadt, L.L.P.

(57) ABSTRACT

Provided is an aqueous composition contained in a container, maintaining an excellent water-evaporation-inhibiting effect even when an alkali metal salt or the like is contained in the aqueous composition, and having excellent long-term stability. The aqueous composition contained in a container includes the following components (A) to (D): (A) a polyoxyethylene alkyl or alkenyl ether having an alkyl or alkenyl group having 20 to 24 carbon atoms and an average molar number of ethylene oxide added of 1.5 to 4, (B) a water-soluble polymer, (C) a nonionic surfactant having an ethylene oxide group (but excluding component (A)), and (D) water.

18 Claims, No Drawings

AQUEOUS COMPOSITION WITH AGENTS TO INHIBIT WATER EVAPORATION

CROSS REFERENCE TO RELATED APPLICATION

This application is a 371 of PCT/JP2011/062062, filed on May 26, 2011, and claims priority to Japanese Patent Application No. 2010-121631, filed on May 27, 2010.

FIELD OF THE INVENTION

The present invention relates to a stable aqueous composition contained in a container, with water evaporation from the aqueous phase inhibited.

BACKGROUND OF THE INVENTION

In the fields of cosmetics, drugs, quasi-drugs, foods, etc., many compositions containing water as a base are used. In such aqueous compositions, in order to prevent evaporation of water from the composition, the compositions are often stored in airtight containers in many cases. However, for example, opening of the lid in daily use causes gradual evaporation of water from an aqueous composition, which may change the physical properties or induce discoloration. In some containers, such as spray containers and pump containers, the discharged content remains at the discharge opening and is dried near the discharge opening. The content adhering to the discharge opening results in a change of color and odor, which makes a feeling upon use worsened. In addition, the content is dried and solidified to cause clogging, and cannot be discharged in some cases, disadvantageously.

In order to suppress such solidification of the content and prevent such clogging of a discharge container, it has been proposed to blend a non-volatile liquid oil with one or more selected from a substance that is solid at 25° C. or less and/or a coating-forming polymer, at a specific ratio (see Patent Document 1). However, a large amount of the non-volatile oil is necessarily blended in order to suppress solidification of the content, which limits possible formulations. In addition, even if the non-volatile oil is blended at a specific ratio, the content is solidified and clogging is not sufficiently prevented.

On the other hand, it has been proposed to improve long-term stability of an emulsion containing a high concentration of alcohol by blending polyoxyethylene behenyl ether having an average number of ethylene oxide added of 5 or more into the emulsion composition (see Patent Documents 2 and 3). Such a method, however, intends to prevent decreases in hardness and viscosity of the emulsion, and effects on water are not known at all.

PRIOR ART LIST

Patent Document

[Patent Document 1] JP-A-2003-321321
[Patent Document 2] JP-A-1989-266844
[Patent Document 3] JP-A-1999-508253

SUMMARY OF THE INVENTION

The present invention provides an aqueous composition contained in a container, wherein the composition contains the following components (A) to (D):

(A) a polyoxyethylene alkyl or alkenyl ether having an alkyl or alkenyl group having 20 to 24 carbon atoms and an average molar number of ethylene oxide added of 1.5 to 4;
(B) a water-soluble polymer;
(C) a nonionic surfactant having an ethylene oxide group (but excluding component (A)); and
(D) water.

The present invention also provides an agent for inhibiting water evaporation of an aqueous composition containing the following components (A) to (C) as active ingredients:

(A) a polyoxyethylene alkyl or alkenyl ether having an alkyl or alkenyl group having 20 to 24 carbon atoms and an average molar number of ethylene oxide added of 1.5 to 4;
(B) a water-soluble polymer; and
(C) a nonionic surfactant having an ethylene oxide group (but excluding component (A)).

The present invention further provides a method of inhibiting water evaporation of an aqueous composition by incorporating a polyoxyethylene alkyl or alkenyl ether (A) having an alkyl or alkenyl group having 20 to 24 carbon atoms and an average molar number of ethylene oxide added of 1.5 to 4, a water-soluble polymer (B), and a nonionic surfactant (C) having an ethylene oxide group (but excluding component (A)) in the aqueous composition.

EMBODIMENTS FOR CARRYING OUT THE INVENTION

The present inventor has conducted various studies for developing an aqueous composition contained in a container, where water evaporation is inhibited to prevent the contents from solidifying or changing in properties and to show excellent long-term stability. Even when the container is a spray container or a pump container, the contents adhering to the discharge opening of the container is inhibited from drying, and thereby clogging can be prevented. As a result, the present inventor has found that a combination of a water-soluble polymer and a polyoxyethylene alkyl or alkenyl ether can considerably inhibit water evaporation of an aqueous composition and that the effect thereof is particularly excellent in the case of using a polyoxyethylene alkyl or alkenyl ether having an alkyl or alkenyl group having 20 to 24 carbon atoms and an average molar number of ethylene oxide added of 1.5 to 4.

In order to apply such an aqueous composition to cosmetics, quasi-drugs, drugs, etc., addition of various aqueous components showing physiological actions, pharmacological actions, and other actions to the aqueous composition has been studied, which unfortunately revealed that a problem of considerably reducing the water-evaporation-inhibiting effect is caused by adding, for example, various alkali metal salts to the aqueous composition.

Accordingly, the present invention relates to provision of an aqueous composition contained in a container that can maintain an excellent water-evaporation-inhibiting effect even when an alkali metal salt or the like is contained in the aqueous composition, and that shows excellent long-term stability.

The present inventor has studied for solving the above-mentioned problems and, as a result, has found that an excellent water-evaporation-inhibiting effect can be obtained by adding a nonionic surfactant having an ethylene oxide group, in addition to a water-soluble polymer and the polyoxyethylene alkyl or alkenyl ether, to an aqueous composition, even when a material preventing water-evaporation-inhibition, such as an alkali metal salt, is added to the aqueous composition. Thus, the present invention has been accomplished.

The present invention provides an aqueous composition having a high water-evaporation-inhibiting effect even when a material preventing water-evaporation-inhibition, such as an alkali metal salt, is added to the aqueous composition and having excellent long-term stability where a change in appearance, such as separation, may be inhibited even in long-period storage. The aqueous composition exhibits and maintains a high water-evaporation-inhibiting effect by containing a small amount of component (A) (hereinafter may also be referred to as polyoxyethylene alkyl ether (A) or POE alkyl ether) and a nonionic surfactant having an ethylene oxide group. Accordingly, the aqueous composition may be used in any formulation and does not affect the feeling upon use.

Preferred embodiments of the composition of the present invention are, for example, as follows:

[1] An aqueous composition contained in a container, containing the following components (A) to (D):
(A) a polyoxyethylene alkyl or alkenyl ether having an alkyl or alkenyl group having 20 to 24 carbon atoms and an average molar number of ethylene oxide added of 1.5 to 4;
(B) a water-soluble polymer;
(C) a nonionic surfactant having an ethylene oxide group (but excluding component (A)); and
(D) water;

[2] An agent for inhibiting water evaporation of an aqueous composition that contains the following components (A) to (C) as active ingredients:
(A) a polyoxyethylene alkyl or alkenyl ether having an alkyl or alkenyl group having 20 to 24 carbon atoms and an average molar number of ethylene oxide added of 1.5 to 4;
(B) a water-soluble polymer; and
(C) a nonionic surfactant having an ethylene oxide group (but excluding component (A));

[3] A method of inhibiting water evaporation of an aqueous composition by incorporating a polyoxyethylene alkyl or alkenyl ether (A) having an alkyl or alkenyl group having 20 to 24 carbon atoms and an average molar number of ethylene oxide added of 1.5 to 4, a water-soluble polymer (B), and a nonionic surfactant (C) having an ethylene oxide group (but excluding component (A)) in the aqueous composition;

[4] The aqueous composition contained in a container according to embodiment [1], the agent for inhibiting water evaporation according to embodiment [2], or the method of inhibiting water evaporation according to embodiment [3], wherein component (A) is a polyoxyethylene alkyl or alkenyl ether having an alkyl or alkenyl group having 20 to 24 carbon atoms and an average molar number of ethylene oxide added of 1.5 to 3;

[5] The aqueous composition contained in a container according to embodiment [1] or [4], the agent for inhibiting water-evaporation according to embodiment [2] or [4], or the method of inhibiting water evaporation according to embodiment [3] or [4], wherein component (A) is a polyoxyethylene alkyl or alkenyl ether having an alkyl or alkenyl group having 20 to 24 carbon atoms and an average molar number of ethylene oxide added of 1.5 to 2.5;

[6] The aqueous composition contained in a container according to any one of embodiments [1], [4], and [5], the agent for inhibiting water evaporation according to any one of embodiments [2], [4], and [5], or the method of inhibiting water evaporation according to any one of embodiments [3], [4], and [5], wherein component (A) is selected from the group consisting of polyoxyethylene(2) arachyl ether, polyoxyethylene(3) arachyl ether, polyoxyethylene(4) arachyl ether, polyoxyethylene(2) behenyl ether, polyoxyethylene(3) behenyl ether, polyoxyethylene(4) behenyl ether, polyoxyethylene(2) carnaubyl ether, polyoxyethylene(3) carnaubyl ether, and polyoxyethylene(4) carnaubyl ether;

[7] The aqueous composition contained in a container according to any one of embodiments [1] and [4] to [6], the agent for inhibiting water evaporation according to any one of embodiments [2] and [4] to [6], or the method of inhibiting water evaporation according to any one of embodiments [3] and [4] to [6], wherein component (A) is a polyoxyethylene alkyl or alkenyl ether having an alkyl or alkenyl group having 21 to 23 carbon atoms and an average molar number of ethylene oxide added of 1.5 to 4;

[8] The aqueous composition contained in a container according to any one of embodiments [1] and [4] to [7], the agent for inhibiting water evaporation according to any one of embodiments [2] and [4] to [7], or the method of inhibiting water evaporation according to any one of embodiments [3] and [4] to [7], wherein component (A) is a polyoxyethylene alkyl or alkenyl ether having an alkyl or alkenyl group having 21 to 23 carbon atoms and an average molar number of ethylene oxide added of 1.5 to 3;

[9] The aqueous composition contained in a container according to any one of embodiments [1] and [4] to [8], the agent for inhibiting water evaporation according to any one of embodiments [2] and [4] to [8], or the method of inhibiting water evaporation according to any one of embodiments [3] and [4] to [8], wherein component (A) is a polyoxyethylene alkyl or alkenyl ether having an alkyl or alkenyl group having 21 to 23 carbon atoms and an average molar number of ethylene oxide added of 1.5 to 2.5;

[10] The aqueous composition contained in a container according to any one of embodiments [1] and [4] to [9], the agent for inhibiting water evaporation according to any one of embodiments [2] and [4] to [9], or the method of inhibiting water evaporation according to any one of embodiments [3] and [4] to [9], wherein component (A) is polyoxyethylene (2) behenyl ether;

[11] The aqueous composition contained in a container according to any one of embodiments [1] and [4] to [10], the agent for inhibiting water evaporation according to any one of embodiments [2] and [4] to [10], or the method of inhibiting water evaporation according to any one of embodiments [3] and [4] to [10], wherein component (A) is contained in an amount of from 0.05 to 20% by mass based on the total amount of the composition;

[12] The aqueous composition contained in a container according to any one of embodiments [1] and [4] to [11], the agent for inhibiting water evaporation according to any one of embodiments [2] and [4] to [11], or the method of inhibiting water evaporation according to any one of embodiments [3] and [4] to [11], wherein component (A) is contained in an amount of from 0.1 to 20% by mass based on the total amount of the composition;

[13] The aqueous composition contained in a container according to any one of embodiments [1] and [4] to [12], the agent for inhibiting water evaporation according to any one of embodiments [2] and [4] to [12], or the method of inhibiting water evaporation according to any one of embodiments [3] and [4] to [12], wherein component (A) is contained in an amount of from 0.1 to 10% by mass based on the total amount of the composition;

[14] The aqueous composition contained in a container according to any one of embodiments [1] and [4] to [13], the agent for inhibiting water evaporation according to any one of embodiments [2] and [4] to [13], or the method of inhibiting water evaporation according to any one of embodiments [3] and [4] to [13], wherein component (B) is one or more selected from the group consisting of carboxyvinyl polymers, alkyl acrylate/methacrylate copolymers, xanthan gum, hydroxypropyl methylcellulose, polyacrylamides, and (sodium acrylate/sodium acryloyl dimethyl taurate) copolymers;

[15] The aqueous composition contained in a container according to any one of embodiments [1] and [4] to [14], the agent for inhibiting water evaporation according to any one of embodiments [2] and [4] to [14], or the method of inhibiting water evaporation according to any one of embodiments [3] and [4] to [14], wherein component (B) is contained in an amount of from 0.01 to 5% by mass based on the total amount of the composition;

[16] The aqueous composition contained in a container according to any one of embodiments [1] and [4] to [15], the agent for inhibiting water evaporation according to any one of embodiments [2] and [4] to [15], or the method of inhibiting water evaporation according to any one of embodiments [3] and [4] to [15], wherein component (B) is contained in an amount of from 0.05 to 3% by mass based on the total amount of the composition;

[17] The aqueous composition contained in a container according to any one of embodiments [1] and [4] to [15], the agent for inhibiting water evaporation according to any one of embodiments [2] and [4] to [15], or the method of inhibiting water evaporation according to any one of embodiments [3] and [4] to [15], wherein component (C) is a nonionic surfactant having an average molar number of ethylene oxide added of 10 or more;

[18] The aqueous composition contained in a container according to any one of embodiments [1] and [4] to [16], the agent for inhibiting water evaporation according to any one of embodiments [2] and [4] to [16], or the method of inhibiting water evaporation according to any one of embodiments [3] and [4] to [16], wherein component (C) is a nonionic surfactant having an average molar number of ethylene oxide added of 10 to 200;

[19] The aqueous composition contained in a container according to any one of embodiments [1] and [4] to [18], the agent for inhibiting water evaporation agent according to any one of embodiments [2] and [4] to [18], or the method of inhibiting water evaporation according to any one of embodiments [3] and [4] to [18], wherein component (C) is one or more selected from the group consisting of polyoxyethylene alkyl ethers, polyoxyethylene alkylphenyl ethers, polyoxyethylene polyoxypropylene alkyl ethers, polyoxyethylene fatty acid esters, polyoxyethylene glycerine fatty acid esters, polyoxyethylene sorbitan fatty acid esters, polyoxyethylene castor oils, polyoxyethylene hydrogenated castor oils, polyoxyalkylene hydrogenated castor oil fatty acid esters, and polyoxyethylene sorbitols;

[20] The aqueous composition contained in a container according to any one of embodiments [1] and [4] to [19], the agent for inhibiting water evaporation according to any one of embodiments [2] and [4] to [19], or the method of inhibiting water evaporation according to any one of embodiments [3] and [4] to [19], wherein component (C) is one or more selected from the group consisting of polyoxyethylene glycerine fatty acid esters, polyoxyethylene sorbitan fatty acid esters, polyoxyethylene castor oils, polyoxyethylene hydrogenated castor oils, and polyoxyalkylene hydrogenated castor oil fatty acid esters;

[21] The aqueous composition contained in a container according to any one of embodiments [1] and [4] to [20], the agent for inhibiting water evaporation according to any one of embodiments [2] and [4] to [20], or the method of inhibiting water evaporation according to any one of embodiments [3] and [4] to [20], wherein component (C) is contained in an amount of from 0.001 to 15% by mass based on the total amount of the composition;

[22] The aqueous composition contained in a container according to any one of embodiments [1] and [4] to [21], the agent for inhibiting water evaporation according to any one of embodiments [2] and [4] to [21], or the method of inhibiting water evaporation according to any one of embodiments [3] and [4] to [21], wherein component (C) is contained in an amount of from 0.005 to 10% by mass based on the total amount of the composition;

[23] The aqueous composition contained in a container according to any one of embodiments [1] and [4] to [22], the agent for inhibiting water evaporation according to any one of embodiments [2] and [4] to [22], or the method of inhibiting water evaporation according to any one of embodiments [3] and [4] to [22], wherein component (C) is contained in an amount of from 0.01 to 5% by mass based on the total amount of the composition;

[24] The aqueous composition contained in a container according to any one of embodiments [1] and [4] to [23], the agent for inhibiting water evaporation according to any one of embodiments [2] and [4] to [23], or the method of inhibiting water evaporation according to any one of embodiments [3] and [4] to [23], wherein the aqueous composition further includes a polyol;

[25] The aqueous composition contained in a container according to any one of embodiments [1] and [4] to [24], the agent for inhibiting water evaporation according to any one of embodiments [2] and [4] to [24], or the method of inhibiting water evaporation according to any one of embodiments [3] and [4] to [24], wherein the aqueous composition further includes component (E): one or more selected from the group consisting of metals of Group 1 in the periodic table, metals of Group 2 in the periodic table, and water-soluble compounds of these metals;

[26] The aqueous composition contained in a container, the agent for inhibiting water evaporation, or the method of inhibiting water evaporation according to embodiment [25], wherein component (E) is one or more selected from the group consisting of sodium, potassium, magnesium, calcium, and water-soluble compounds thereof;

[27] The aqueous composition contained in a container according to any one of embodiments [1] and [4] to [26], wherein the aqueous composition is in a formulation of an aqueous solution or an emulsification system in which continuous phase is an aqueous phase; and

[28] The aqueous composition contained in a container according to any one of embodiments [1] and [4] to [27], the aqueous composition being used for a cosmetic, drug, quasi-drug, or food.

The aqueous composition in the present invention is a composition having an aqueous phase as a continuous phase, and encompasses a water-soluble composition containing a water-soluble component, an oil-in-water emulsion composition containing water in the continuous phase, and a W/O/W emulsion composition.

The aqueous phase in the present invention is a phase containing water.

In the present invention, the material preventing water-evaporation-inhibition is a material that considerably increases the water evaporation rate of an aqueous composition including polyoxyethylene alkyl ether (A), a water-soluble polymer, and water when the material is added to the aqueous composition. For example, in the test described in Example (test 1), if the water evaporation rate of the composition shown in Table 1 is higher by 10 mg/h or more, compared with a composition being the same as the composition of Table 1 except that the test material is not contained, the test material is recognized as a material preventing water-evaporation-inhibition in the present invention.

TABLE 1

| | |
|---|---|
| Polyoxyethylene(2) behenyl ether | 1% by mass |
| Dipropylene glycol | 5% by mass |
| Carboxyvinyl polymer | 0.1% by mass |
| 10% Potassium hydroxide | 0.37% by mass |
| Test material | 0.1% by mass |
| Methyl parahydroxybenzoate | 0.1% by mass |
| Pure water | balance |

In particular, for metals (alkali metals) of Group 1 in the periodic table, metals of Group 2 in the periodic table, and water-soluble compounds of these metals, addition of such a metal or compound to an aqueous composition containing polyoxyethylene alkyl ether (A) and a water-soluble polymer causes a phenomenon that a water-evaporation-inhibiting effect is considerably decreased.

In particular, in the fields of drugs and cosmetics, in light of adaptability to the human body, influences of prevention of water-evaporation-inhibition by especially sodium, potassium, magnesium, calcium, and water-soluble compounds thereof are important. Specific examples of such substance include water-soluble sodium salts of organic acids, water-soluble sodium salts of inorganic acids, sodium halides, sodium hydroxide, water-soluble potassium salts of organic acids, water-soluble potassium salts of inorganic acids, potassium halides, potassium hydroxide, water-soluble magnesium salts of organic acids, water-soluble magnesium salts of inorganic acids, magnesium halides, magnesium hydroxide, water-soluble calcium salts of organic acids, water-soluble calcium salts of inorganic acids, calcium halides, and calcium hydroxide.

More specifically, the examples are sodium ascorbate, disodium ascorbyl sulfate, sodium alginate, sodium benzoate, disodium edetate, trisodium edetate, tetrasodium edetate, disodium calcium edetate, sodium chloride, sodium citrate, disodium citrate, sodium glycyrrhizinate, disodium glycyrrhetinate, sodium glutamate, disodium succinate, sodium hydroxide, sodium sorbate, sodium bicarbonate, sodium carbonate, sodium dehydroacetate, sodium metasilicate, sodium metaphosphate, tetrasodium hydroxyethanediphosphonate, sodium pyrophosphate, sodium pyrosulfite, sodium hexametaphosphate, sodium polyphosphate, sodium sulfate, sodium sulfite, sodium hydrogen sulfite, monosodium phosphate, sodium dihydrogen phosphate, disodium hydrogen phosphate, trisodium phosphate, potassium ascorbate, dipotassium ascorbyl sulfate, potassium alginate, potassium benzoate, dipotassium edetate, tripotassium edetate, tetrapotassium edetate, dipotassium calcium edetate, potassium chloride, potassium citrate, dipotassium citrate, potassium glycyrrhizinate, dipotassium glycyrrhetinate, potassium glutamate, dipotassium succinate, potassium hydroxide, potassium sorbate, potassium bicarbonate, potassium carbonate, potassium dehydroacetate, potassium metasilicate, potassium metaphosphate, tetrapotassium hydroxyethanediphosphonate, potassium pyrophosphate, potassium pyrosulfite, potassium hexametaphosphate, potassium polyphosphate, potassium sulfate, potassium sulfite, potassium hydrogen sulfite, monopotassium phosphate, potassium dihydrogen phosphate, dipotassium hydrogen phosphate, tripotassium phosphate, calcium chloride, calcium hydroxide, calcium acetate, calcium carbonate, calcium thioglycolate, magnesium sulfate, magnesium chloride, magnesium hydroxide, magnesium acetate, magnesium carbonate, magnesium thioglycolate, and magnesium sulfate. A material preventing water-evaporation-inhibition contains one or more of these compounds.

The content of these materials preventing water-evaporation-inhibition in the aqueous composition is not particularly limited, but is 0.0001% by mass or more in light of various medicinal benefits and actions, preferably from 0.0001 to 10% by mass, which sufficiently shows various medicinal benefits and actions.

In the polyoxyethylene alkyl ether (A) used in the present invention, the alkyl or alkenyl group has 20 to 24 carbon atoms, and the average molar number of ethylene oxide added is 1.5 to 4.

The alkyl or alkenyl group of the polyoxyethylene alkyl ether (A) may be a linear chain or a branched chain without limiting the structure thereof, but is preferably a linear or branched alkyl group and more preferably a linear alkyl group. The alkyl or alkenyl group has 20 to 24 carbon atoms, preferably 21 to 23 carbon atoms, and even more preferably 22 carbon atoms, i.e., a behenyl group. An alkyl or alkenyl group having less than 20 carbon atoms has a low water-evaporation inhibiting effect and is therefore not preferred. An alkyl or alkenyl group having higher than 24 carbon atoms is difficult to be dissolved in an aqueous phase and is therefore not preferred from the viewpoint of formulation.

The polyoxyethylene alkyl ether (A) has an average molar number of ethylene oxide added in the range of 1.5 to 4, preferably 1.5 to 3, and even more preferably 1.5 to 2.5. An average molar number of ethylene oxide added of less than 1.5 causes high crystallizability and difficulty in dissolving in an aqueous phase and is therefore not preferred. An average molar number of ethylene oxide added of higher than 4 notably decreases the water-evaporation inhibiting effect and is therefore not preferred. Polyoxyethylene alkyl ethers (A) that can be generally available are each a mixture having a significantly broad distribution of the molar number of ethylene oxide added with a desired degree of polymerization at the center, but it is important in the present invention to have the average molar number of ethylene oxide added in the above-mentioned range.

Chief examples of the polyoxyethylene alkyl ether (A) of the present invention include polyoxyethylene(2) arachyl ether, polyoxyethylene(3) arachyl ether, polyoxyethylene(4) arachyl ether, polyoxyethylene(2) behenyl ether, polyoxyethylene(3) behenyl ether, polyoxyethylene(4) behenyl ether, polyoxyethylene(2) carnaubyl ether, polyoxyethylene(3) carnaubyl ether, and polyoxyethylene(4) carnaubyl ether; and preferably polyoxyethylene(2) behenyl ether, polyoxyethylene(3) behenyl ether, and polyoxyethylene(4) behenyl ether. In addition, a polyoxyethylene alkyl ether other than those mentioned above can be concomitantly used as long as the polyoxyethylene alkyl ether has an average molar number of ethylene oxide added in the above-mentioned range.

The content of the polyoxyethylene alkyl ether (A) in the aqueous composition of the present invention is preferably from 0.05 to 20% by mass, more preferably from 0.1 to 20% by mass, and even more preferably from 0.1 to 10% by mass, based on the total amount of the composition. A content within the range can provide high water-evaporation inhibiting effect and allows blending with an aqueous phase and is therefore preferred.

The aqueous composition of the present invention contains a water-soluble polymer (B). The water-soluble polymer allows the polyoxyethylene alkyl ether (A) to stably disperse in an aqueous phase and contributes to the water-evaporation inhibiting effect. Examples of the water-soluble polymer used in the present invention include water-soluble cationic, anionic, nonionic, amphoteric, and bipolar polymers.

Specific examples of the cationic polymers include poly (dimethyl diallyl ammonium halide) cationic polymers, cationic copolymers of dimethyl diallyl ammonium halide and acrylamide, and quaternary nitrogen-containing cellulose ether, and condensation products of polyethylene glycol, epichlorohydrin, propylene amine, and tallowyl amine obtained from tallow fatty acids, and cationized products of vinylpyrrolidone/dimethylaminoethyl methacrylate copolymers, and commercially available examples of the poly(dimethyl diallyl ammonium halide) cationic polymers include Merquat 100, a trade name, available from Merck & Co., Inc., U.S.A. Commercially available examples of the cationic copolymers of dimethyl diallyl ammonium halide and acrylamide include Merquat 550 (Merquat & Co., Inc., U.S.A.). Commercially available examples of the condensation products of polyethylene glycol, epichlorohydrin, propylene amine, and tallowyl or cocoyl amine include Polyquat H, a trade name, available from Henkel International Co., Germany. Commercially available examples of the quaternary nitrogen-containing cellulose include Polymer JR-400, Polymer JR-125, and Polymer JR-30M, trade names, available from Union Carbide Corp., U.S.A. Commercially available examples of the cationized products of vinylpyrrolidone/dimethylaminoethyl methacrylate copolymers include Gafquat 755 and Gafquat 734, trade names, available from GAF Corp., U.S.A.

Specific examples of the anionic polymers include carboxyvinyl polymers, carboxymethyl cellulose, carageenan, xanthan gum, polystyrene sulfonate, agar, Gatti gum, karaya gum, pectin, alginate salts, as well as poly(acrylic acid), and acrylic or methacrylic acid derivatives such as alkali metal salts and ammonium salts of acrylic acid and methacrylic acid.

Specific examples of the nonionic polymers include cellulose ethers (e.g., hydroxybutyl methylcellulose, hydroxypropyl cellulose, hydroxypropyl methylcellulose, ethylhydroxyethyl cellulose, and hydroxyethyl cellulose), propylene glycol alginate, polyacrylamide, (sodium acrylate/sodium acryloyl dimethyl taurate) copolymers, poly(ethylene oxide), polyvinyl alcohol, polyvinylpyrrolidone, hydroxypropyl guar gum, locust bean gum, amylose, hydroxyethyl amylose, hyaluronic acid and alkali metal salts thereof, starch, and starch derivatives, and mixtures thereof.

Specific examples of the amphoteric polymers and the bipolar polymers include octyl acrylamide/acrylate/butylaminoethyl methacrylate copolymers, polyquaternium-47, and polyquaternium-43.

These water-soluble polymers may be used either alone or in combination with two or more. Preferred from the viewpoint of application to various formulations are carboxyvinyl polymers, alkyl acrylate/methacrylate copolymers, xanthan gum, hydroxypropyl methylcellulose, polyacrylamide, (sodium acrylate/sodium acryloyl dimethyl taurate) copolymers, and hyaluronic acid and alkali metal salts thereof.

The content of the water-soluble polymer used in the present invention is preferably from 0.01 to 5% by mass, more preferably from 0.05 to 3% by mass, based on the total amount of the composition. A content within the range can maintain stability of a pharmaceutical preparation and provide excellent water-evaporation inhibiting effect and is therefore preferred.

Examples of the nonionic surfactant (C) having an ethylene oxide group (but excluding the polyoxyethylene alkyl ether (A)) used in the present invention include ether-type and ester-type surfactants. Examples of the ether-type surfactant include polyoxyethylene alkyl ethers, polyoxyethylene alkylphenyl ethers, and polyoxyethylene polyoxypropylene alkyl ethers. Examples of the ester-type surfactant include polyoxyethylene fatty acid esters, polyoxyethylene glycerine fatty acid esters, polyoxyethylene sorbitan fatty acid esters, polyoxyethylene castor oils, polyoxyethylene hydrogenated castor oils, polyoxyalkylene hydrogenated castor oil fatty acid esters, and polyoxyethylene sorbitols. Among these nonionic surfactants, the ester type is preferred from feeling upon use and safety. Particularly preferred are polyoxyethylene glycerine fatty acid esters, polyoxyethylene sorbitan fatty acid esters, polyoxyethylene castor oils, polyoxyethylene hydrogenated castor oils, and polyoxyalkylene hydrogenated castor oil fatty acid esters.

The nonionic surfactant having an ethylene oxide group preferably has an average molar number of ethylene oxide added of 10 or more, more preferably from 10 to 200, even more preferably from 20 to 200, further more preferably from 30 to 140, and even more preferably 40 to 120. An average molar number of ethylene oxide added within the range is preferable to provide less skin irritation, an excellent water-evaporation-inhibiting effect, and high long-term stability.

Preferred examples of the nonionic surfactant having an ethylene oxide group include polyoxyethylene(40) glyceryl trioleate, polyoxyethylene(50) glyceryl trioleate, polyoxyethylene(60) glyceryl trioleate, polyoxyethylene(45) glyceryl monostearate, polyoxyethylene(50) glyceryl monostearate, polyoxyethylene(75) glyceryl monostearate, polyoxyethylene(90) glyceryl monostearate, polyoxyethylene(100) glyceryl monostearate, polyoxyethylene(120) glyceryl monostearate, polyoxyethylene(40) glyceryl monoisostearate, polyoxyethylene(40) glyceryl triisostearate, polyoxyethylene(50) glyceryl triisostearate, polyoxyethylene(60) glyceryl triisostearate, polyoxyethylene(120) sorbitan tristearate, polyoxyethylene(40) castor oil, polyoxyethylene(50) castor oil, polyoxyethylene(60) castor oil, polyoxyethylene(75) castor oil, polyoxyethylene(100) castor oil, polyoxyethylene(40) hydrogenated castor oil, polyoxyethylene(50) hydrogenated castor oil, polyoxyethylene(60) hydrogenated castor oil, polyoxyethylene(80) hydrogenated castor oil, polyoxyethylene(100) hydrogenated castor oil, polyoxyethylene(40) hydrogenated castor oil monolaurate, polyoxyethylene(50) hydrogenated castor oil monolaurate, polyoxyethylene(60) hydrogenated castor oil monolaurate, polyoxyethylene(40) hydrogenated castor oil monostearate, polyoxyethylene(50) hydrogenated castor oil monostearate, polyoxyethylene(40) hydrogenated castor oil monoisostearate, polyoxyethylene(50) hydrogenated castor oil monoisostearate, polyoxyethylene(60) hydrogenated castor oil monoisostearate, polyoxyethylene(40) hydrogenated castor oil tristearate, polyoxyethylene(50) hydrogenated castor oil tristearate, and polyoxyethylene(60) hydrogenated castor oil tristearate. These nonionic surfactants can be used either alone or in combination with two or more.

The content of the nonionic surfactant (C) having an ethylene oxide group used in the present invention is preferably from 0.001 to 15% by mass, more preferably from 0.005 to 10% by mass, and even more preferably from 0.01 to 5% by mass, based on the total amount of the composition. A content of the nonionic surfactant (C) within the range is preferable to provide less skin irritation and a satisfactory water-evaporation-inhibiting effect.

The content mass ratio of the nonionic surfactant having an ethylene oxide group to the material preventing water-evaporation-inhibition is preferably from 1:20 to 50:1, more preferably from 1:12 to 20:1, and even more preferably from 1:4 to 15:1. A content mass ratio within the range is preferable to provide a satisfactory water-evaporation-inhibiting effect.

The composition of the present invention preferably further contains a polyol in order to enhance the solubility of the polyoxyethylene alkyl ether (A) in an aqueous phase. Preferred examples of the polyol include a glycol such as ethylene glycol, diethylene glycol, triethylene glycol, polyethylene glycol (average molecular weight: less than 1000), propylene glycol, dipropylene glycol, polypropylene glycol (average molecular weight: less than 1000), isoprene glycol, and 1,3-butylene glycol; and glycerine, diglycerine, and polyglycerine.

The content of a polyol used together with the polyoxyethylene alkyl ether (A) is preferably 0.5 to 50 times, more preferably 1 to 35 times, and even more preferably 1 to 20 times the content of the polyoxyethylene alkyl ether (A) as the mass ratio. A content of the polyol within the range is preferable to make the solubility of the polyoxyethylene alkyl ether (A) satisfactory and to provide a satisfactory water-evaporation-inhibiting effect.

The composition of the present invention can contain, in addition to the above-mentioned essential components, higher alcohols, fatty acids, esters, sterols, sterol-fatty acid esters, hydrocarbons, fats and oils, silicone oils, moisturizing agents, plant extracts, vitamins, oxidation inhibitors, antibacterial antiseptic agents, antiphlogistics, insect repellents, physiologically active ingredients, salts, chelating agents, neutralizers, pH adjusters, flavors, etc., within a range that does not impair the purpose of the present invention.

The content of water in the aqueous composition of the present invention may be any level that allows formation of an aqueous solution or an emulsification system having a continuous phase of an aqueous phase such as an O/W system or a W/O/W system, and is preferably 10% by mass or more, more preferably 15% by mass or more, and even more preferably 20% by mass or more.

Even if the aqueous composition of the present invention is a liquid having a low viscosity (at 25° C.) of 100 mPa·s or less, a high water-evaporation inhibiting effect can be provided as long as the stability of a pharmaceutical preparation is maintained.

The formulation of the aqueous composition of the present invention is not particularly limited as long as the aqueous phase is the continuous phase and can be, for example, emulsion, gel, spray, or mousse.

Use of the aqueous composition of the present invention is not particularly limited, and preferred examples of the use include cosmetics, drugs, quasi-drugs, and foods (including health foods). Specifically, the aqueous composition of the present invention can be suitably used as hair cosmetics such as shampoo, rinse, and conditioners; and skin cosmetics such as facial cleansers, cleansing cosmetics, sunscreen cosmetics, facial packs, and massage cosmetics.

The container used in the present invention has a certain degree of sealability and is not particularly limited as long as it can be suitably used for the above-mentioned uses, including bottles with lids, jar bottles, tubes, spray containers, pump containers, and pump foamer containers. These containers filled with the aqueous composition can be used.

In particular, when a discharge container, such as a spray container, pump container, or pump foamer container, filled with the aqueous composition of the present invention is used, even if the composition contains solid lipid or powder that tends to readily solidify, deterioration (change in color and/or odor) at the discharge opening and clogging can be prevented. Thus, the aqueous composition can be suitably used.

EXAMPLES

The present invention will now be more specifically described by examples and comparative examples, but is not limited to the following examples. Note that the amount of each component is expressed in % by mass.

Test 1: Water-Evaporation Inhibiting Effect of Polyoxyethylene Alkyl Ether (A)

Five grams of each of samples 1 to 14 having components shown in Table 2 were placed in respective dishes having an opening area of 13.85 cm$^2$ and were left at a humidity of 30% and a temperature of 30° C. Changes in weight of each sample were measured 1, 3, 5, 7, 12, 18, and 24 hr later. The slope of the changes in weight, the n of nX+m (X represents time (hr)) calculated by a least-squares method, was defined as the water evaporation rate (unit: mg/h), and the absolute value thereof was plotted. The test was conducted three times for each sample, and the average value thereof was determined. Note that a lower water evaporation rate means higher inhibition of evaporation.

TABLE 2

| (Component) | Content (%) |
| --- | --- |
| POE alkyl ether shown in Table 3 | 1 |
| 2% Carboxyvinyl polymer (Synthalen K, manufactured by Wako Pure Chemical Industries, Ltd.) | 5 |
| 10% Potassium hydroxide | 0.37 |
| Methyl parahydroxybenzoate | 0.1 |
| Pure water | balance |

TABLE 3

| | POE alkyl ether | | Average molar number of ethylene oxide added | Water evaporation rate (mg/h) |
| --- | --- | --- | --- | --- |
| | Alkyl group | Carbon number | | |
| Sample 1 | Lauryl | C12 | 2 | 134 |
| Sample 2 | Cetyl | C16 | 2 | 88 |
| Sample 3 | Stearyl | C18 | 2 | 80 |
| Sample 4 | Oleyl | C18 | 2 | 128 |
| Sample 5 | Behenyl | C22 | 2 | 41 |
| Sample 6 | Mixture | C12 to 15 | 2 | 118 |
| Sample 7 | Isostearyl | C18 | 2 | 125 |
| Sample 8 | Lauryl | C12 | 4 | 121 |
| Sample 9 | Cetyl | C16 | 5.5 | 116 |
| Sample 10 | Stearyl | C18 | 4 | 77 |
| Sample 11 | Oleyl | C18 | 4 | 122 |
| Sample 12 | Behenyl | C22 | 5 | 120 |
| Sample 13 | Mixture | C12 to 15 | 4 | 125 |
| Sample 14 | Isostearyl | C18 | 4 | 123 |

Test 1 reveals that polyoxyethylene behenyl ether having an average molar number of ethylene oxide added of 1.5 to 4, in particular, 2 shows an excellent water evaporative inhibiting effect, compared with other polyoxyethylene alkyl ethers including polyoxyethylene behenyl ether having an average molar number of ethylene oxide added of 5.

Test 2: Water-Evaporation-Inhibiting Effect

The components of Examples 1 to 5, Comparative Examples 1 to 7, and control shown in Tables 4 and 5 were measured for water evaporation rates as in Test 1. The water evaporation inhibition ratio was defined on the basis of the control (control in Table 5) as follows.

Water evaporation inhibition ratio(%)={1−(water evaporation rate of Example or Comparative Example)/(water evaporation rate of control)}×100

TABLE 4

| Component | Example 1 | Example 2 | Example 3 | Example 4 | Example 5 |
|---|---|---|---|---|---|
| 1 Polyoxyethylene(2) behenyl ether | 1 | 1 | 1 | 1 | 1 |
| 2 Polyoxyethylene(5) behenyl ether | — | — | — | — | — |
| 3 Polyoxyethylene glycol 4000 | 5 | 5 | 5 | 5 | 5 |
| 4 Glycerine | 5 | 5 | 5 | 5 | 5 |
| 5 POE(60) hydrogenated castor oil | 0.02 | 0.04 | | 0.1 | |
| 6 POE(100) hydrogenated castor oil | | | 0.04 | | 0.1 |
| 7 Disodium edetate | 0.02 | | | | |
| 8 Sodium citrate | | 0.02 | | | |
| 9 Monosodium phosphate | | | 0.02 | | |
| 10 Sodium sulfate | | | | 0.02 | |
| 11 Dipotassium glycyrrhizinate | | | | | 0.1 |
| 12 Carboxyvinyl polymer *1 | 0.44 | 0.44 | 0.44 | 0.44 | 0.44 |
| 13 10% Potassium hydroxide | 2 | 2 | 2 | 2 | 2 |
| 14 Dipropylene glycol | 5 | 5 | 5 | 5 | 5 |
| 15 Pure water | balance | balance | balance | balance | balance |
| Water evaporation rate (mg/h) | 41 | 40 | 42 | 42 | 45 |
| Water evaporation inhibition ratio (%) | 66.4% | 67.2% | 65.6% | 65.6% | 63.1% |

*1: Synthalen K, manufactured by Wako Pure Chemical Industries, Ltd.

TABLE 5

| Component | Comparative Example 1 | Comparative Example 2 | Comparative Example 3 | Comparative Example 4 | Comparative Example 5 | Comparative Example 6 | Comparative Example 7 | Control |
|---|---|---|---|---|---|---|---|---|
| 1 Polyoxyethylene(2) behenyl ether | 1 | 1 | 1 | 1 | 1 | — | 1 | — |
| 2 Polyoxyethylene(5) behenyl ether | — | — | — | — | — | 1 | — | — |
| 3 Polyoxyethylene glycol 4000 | 5 | 5 | 5 | 5 | 5 | 5 | 5 | 5 |
| 4 Glycerine | 5 | 5 | 5 | 5 | 5 | 5 | 5 | 5 |
| 5 POE(60) hydrogenated castor oil | — | — | — | — | — | — | — | — |
| 6 POE(100) hydrogenated castor oil | — | — | — | — | — | — | — | — |
| 7 Disodium edetate | 0.02 | | | | | | | |
| 8 Sodium citrate | | 0.02 | | | | | | |
| 9 Monosodium phosphate | | | 0.02 | | | | | |
| 10 Sodium sulfate | | | | 0.02 | | | | |
| 11 Dipotassium glycyrrhizinate | | | | | 0.1 | 0.1 | | |
| 12 Carboxyvinyl polymer *1 | 0.44 | 0.44 | 0.44 | 0.44 | 0.44 | 0.44 | 0.44 | 0.44 |
| 13 10% Potassium hydroxide | 2 | 2 | 2 | 2 | 2 | 2 | 2 | 2 |
| 14 Dipropylene glycol | 5 | 5 | 5 | 5 | 5 | 5 | 5 | 5 |
| 15 Pure water | balance | balance | balance | balance | balance | balance | balance | balance |
| Water evaporation rate (mg/h) | 75 | 83 | 90 | 102 | 117 | 115 | 41 | 122 |
| Water evaporation inhibition ratio (%) | 38.5% | 32.0% | 26.2% | 16.4% | 4.1% | 5.7% | 66.4% | — |

*1: Synthalen K, manufactured by Wako Pure Chemical Industries, Ltd.

Manufacturing Process

Components (1) and (2) and component (14) are uniformly mixed to prepare component A. Components (3) to (13), and (15) are gradually added to component A, and the mixture is uniformly mixed to prepare component B.

Test 2 reveals that combination use (Comparative Example 7) of the polyoxyethylene alkyl ether (A) and the water-soluble polymer inhibits water evaporation (41 mg/h) compared with the control (122 mg/h). However, this water-evaporation-inhibiting effect decreases by addition of an alkali metal salt or the like (Comparative Examples 1 to 6). Test 2 reveals that addition of a nonionic surfactant having an ethylene oxide group improves this decrease in water-evaporation-inhibiting effect by the material preventing water-evaporation-inhibition to a level when the material preventing water-evaporation-inhibition is not added.

Test 3: Concentration Dependency on the Water-Evaporation-Inhibiting Effect of Nonionic Surfactant Having an Ethylene Oxide Group Changes in weight of samples of Examples 6 to 11 and Comparative Examples 8 and 9 shown in Table 6 were measured under the same conditions as in Tests 1 and 2, and water evaporation rates and water evaporation inhibition ratios were determined.

TABLE 6

| Component | Example 6 | Example 7 | Example 8 | Example 9 | Example 10 | Example 11 | Comparative Example 8 | Comparative Example 9 | Control |
|---|---|---|---|---|---|---|---|---|---|
| 1 Polyoxyethylene(2) behenyl ether | 1 | 1 | 1 | 1 | 1 | 1 | 1 | 1 | — |
| 2 POE(60) hydrogenated castor oil | 0.01 | 0.02 | 0.05 | 0.1 | 0.5 | 1 | — | — | — |
| 3 Dipotassium glycyrrhizinate | 0.1 | 0.1 | 0.1 | 0.1 | 0.1 | 0.1 | — | 0.1 | — |
| 4 Carboxyvinyl polymer *1 | 0.1 | 0.1 | 0.1 | 0.1 | 0.1 | 0.1 | 0.1 | 0.1 | 0.1 |
| 5 10% Potassium hydroxide | 0.37 | 0.37 | 0.37 | 0.37 | 0.37 | 0.37 | 0.37 | 0.37 | 0.37 |
| 6 Dipropylene glycol | 5 | 5 | 5 | 5 | 5 | 5 | 5 | 5 | 5 |
| 7 Methyl parahydroxybenzoate | 0.1 | 0.1 | 0.1 | 0.1 | 0.1 | 0.1 | 0.1 | 0.1 | 0.1 |
| 8 Pure water | balance | balance | balance | balance | balance | balance | balance | balance | balance |
| Water evaporation rate (mg/h) | 60 | 42 | 41 | 42 | 41 | 42 | 40 | 115 | 123 |
| Water evaporation inhibition ratio (%) | 51.2% | 65.9% | 66.7% | 65.9% | 66.7% | 65.9% | 67.5% | 6.5% | — |
| Presence of precipitation of POE (2) behenyl ether | No | No | No | No | No | No | No | No | — |

*1: Synthalen K, manufactured by Wako Pure Chemical Industries, Ltd.

Manufacturing Process

Component (1) and component (6) are uniformly mixed to prepare component A. Components (2) to (5), (7), and (8) are gradually added to component A, and the mixture is uniformly mixed to prepare component B.

Test 3 reveals that addition of POE hydrogenated castor oil having an ethylene oxide group in an amount of about one-tenth of the amount of potassium glycyrrhizinate serving as a material preventing water-evaporation-inhibition enhances the water-evaporation-inhibiting effect, and in an amount of about one-fifth, the water-evaporation-inhibiting effect is improved to a level when the material preventing water-evaporation-inhibition is not contained.

The invention claimed is:

1. A method of inhibiting water evaporation of an aqueous composition, comprising: incorporating, into an aqueous composition,
    (A) a polyoxyethylene alkyl or alkenyl ether having an alkyl or alkenyl group having 20 to 24 carbon atoms and an average molar number of ethylene oxide added of 1.5 to 4;
    (B) a water-soluble polymer;
    (C) a nonionic surfactant having an ethylene oxide group (but excluding component (A));
    (D) water; and
    (E) at least one member selected from the group consisting of a metal of Group 1 in the periodic table, a metal of Group 2 in the periodic table, and a water-soluble compound of these metals,
    wherein a content mass ratio of component (C) to component (E) is from 1:20 to 50:1.

2. The method according to claim 1, wherein component (A) is a polyoxyethylene alkyl or alkenyl ether having an alkyl or alkenyl group having 20 to 24 carbon atoms and an average molar number of ethylene oxide added of 1.5 to 2.5.

3. The method according to claim 1, wherein component (A) is present in the aqueous composition in an amount of from 0.05 to 20% by mass based on the total amount of the aqueous composition.

4. The method according to claim 1, wherein component (B) is at least one selected from the group consisting of carboxyvinyl polymers, alkyl acrylate/methacrylate copolymers, xanthan gum, hydroxypropyl methylcellulose, polyacrylamides, and (sodium acrylate/sodium acryloyl dimethyl taurate) copolymers.

5. The method according to claim 1, wherein component (B) is present in the aqueous composition in an amount of from 0.01 to 5% by mass based on the total amount of the aqueous composition.

6. The method according to claim 1, wherein component (C) is a nonionic surfactant having an average molar number of ethylene oxide added of 10 or more.

7. The method according to claim 1, wherein component (C) is a nonionic surfactant having an average molar number of ethylene oxide added of 10 to 200.

8. The method according to claim 1, wherein component (C) is at least one selected from the group consisting of polyoxyethylene alkyl ethers, polyoxyethylene alkylphenyl ethers, polyoxyethylene polyoxypropylene alkyl ethers, polyoxyethylene fatty acid esters, polyoxyethylene glycerine fatty acid esters, polyoxyethylene sorbitan fatty acid esters, polyoxyethylene castor oils, polyoxyethylene hydrogenated castor oils, polyoxyalkylene hydrogenated castor oil fatty acid esters, and polyoxyethylene sorbitols.

9. The method according to claim 1, wherein component (C) is at least one selected from the group consisting of polyoxyethylene glycerine fatty acid esters, polyoxyethylene sorbitan fatty acid esters, polyoxyethylene castor oils, polyoxyethylene hydrogenated castor oils, and polyoxyalkylene hydrogenated castor oil fatty acid esters.

10. The method according to claim 1, wherein component (C) is contained in an amount of from 0.001 to 15% by mass based on the total amount of the composition.

11. The method according to claim 1, wherein the aqueous composition further comprises a polyol.

12. The method according to claim 1, wherein component (E) is at least one selected from the group consisting of sodium, potassium, magnesium, calcium, and water-soluble compounds thereof.

13. The method according to claim 1, wherein the aqueous composition is in a form of an aqueous solution or an emulsion having an aqueous phase as a continuous phase.

14. The method according to claim 1, wherein the aqueous composition comprises a cosmetic, drug, quasi-drug, or food.

15. The method according to claim 1, wherein the content mass ratio of component (C) to component (E) is 1:12 to 20:1.

16. The method according to claim 1, wherein the content mass ratio of component (C) to component (E) is 1:4 to 15:1.

17. An aqueous composition present in a container, comprising:
    (A) a polyoxyethylene alkyl or alkenyl ether having an alkyl or alkenyl group having 20 to 24 carbon atoms and an average molar number of ethylene oxide added of 1.5 to 4;

(B) a water-soluble polymer;
(C) a nonionic surfactant having an ethylene oxide group (but excluding component (A));
(D) water; and
(E) at least one selected from the group consisting of metals of Group 1 in the periodic table, metals of Group 2 in the periodic table, and water-soluble compounds of these metals,
wherein a content mass ratio of component (C) to component (E) is 1:20 to 50:1.

18. The method according to claim 1, wherein component (A) comprises a polyoxyethylene alkyl ether derived from behenyl alcohol and component (C) comprises a polyoxyethylene hydrogenated castor oil.

\* \* \* \* \*